(12) United States Patent
Vidlund et al.

(10) Patent No.: US 10,779,937 B2
(45) Date of Patent: *Sep. 22, 2020

(54) TRANSCATHETER HEART VALVE WITH PLICATION WINDOW AND TISSUE ANCHORS

(71) Applicant: VDYNE, LLC, Dallas, TX (US)

(72) Inventors: Robert Vidlund, Forest Lake, MN (US); Mark Christianson, Plymouth, MN (US); David Holtan, Eden Prairie, MN (US); Cameron Vidlund, Forest Lake, MN (US)

(73) Assignee: VDYNE, INC., Maple Grove, MN (US)

( * ) Notice: Subject to any disclaimer, the term of this patent is extended or adjusted under 35 U.S.C. 154(b) by 202 days.

This patent is subject to a terminal disclaimer.

(21) Appl. No.: 16/016,484

(22) Filed: Jun. 22, 2018

(65) Prior Publication Data

US 2019/0388220 A1 Dec. 26, 2019

(51) Int. Cl.
*A61F 2/24* (2006.01)

(52) U.S. Cl.
CPC .......... *A61F 2/2418* (2013.01); *A61F 2/2427* (2013.01); *A61F 2210/0014* (2013.01); *A61F 2220/0008* (2013.01); *A61F 2220/0016* (2013.01); *A61F 2230/001* (2013.01); *A61F 2230/0017* (2013.01); *A61F 2230/0019* (2013.01); *A61F 2250/0067* (2013.01); *A61F 2250/0098* (2013.01)

(58) Field of Classification Search
CPC ........ A61F 2/24; A61F 2/2412; A61F 2/2427; A61F 2/2466
See application file for complete search history.

(56) References Cited

U.S. PATENT DOCUMENTS

| | | | |
|---|---|---|---|
| 6,254,636 B1 * | 7/2001 | Peredo | A61F 2/2412 623/2.15 |
| 7,331,991 B2 | 2/2008 | Kheradvar et al. | |
| 7,374,571 B2 | 5/2008 | Pease et al. | |
| 7,753,949 B2 | 7/2010 | Lamphere et al. | |
| 9,579,196 B2 | 2/2017 | Morriss et al. | |
| 9,895,219 B2 | 2/2018 | Costello | |
| 9,968,445 B2 | 5/2018 | Kheradvar | |
| 9,980,815 B2 | 5/2018 | Nitzan et al. | |
| 10,022,222 B2 | 7/2018 | Groothuis et al. | |
| 10,028,821 B2 | 7/2018 | Centola et al. | |
| 10,034,667 B2 | 7/2018 | Morris et al. | |
| 10,034,747 B2 | 7/2018 | Harewood | |
| 10,039,638 B2 | 8/2018 | Bruchman et al. | |
| 10,058,411 B2 | 8/2018 | Fifer et al. | |
| 10,058,421 B2 | 8/2018 | Eberhardt et al. | |
| 10,058,426 B2 | 8/2018 | Barbarino | |

(Continued)

*Primary Examiner* — Gregory A Anderson
(74) *Attorney, Agent, or Firm* — Juneau & Mitchell IP Law Firm; Todd L. Juneau

(57) ABSTRACT

The invention relates to a transcatheter heart valve replacement (A61F2/2412), and in particular a device and method for percutaneous annular plication, as a replacement device for a heart valve, whereby the prosthesis has an atrial annular flange or cuff having one or more integral plication windows connected to a pressure actuated flow control member extending into the ventricle, wherein the is a reciprocating mechanical member that is compressed by pressurized working fluid within the heart during ventricular systole.

17 Claims, 8 Drawing Sheets

(56) References Cited

U.S. PATENT DOCUMENTS

| | | |
|---|---|---|
| 10,085,835 B2 | 10/2018 | Thambar et al. |
| 2007/0244558 A1* | 10/2007 | Machiraju ............ A61F 2/2409 623/2.18 |
| 2010/0049313 A1 | 2/2010 | Alon et al. |
| 2010/0179647 A1 | 7/2010 | Carpenter et al. |
| 2010/0298930 A1* | 11/2010 | Orlov ................ A61B 17/3421 623/2.11 |
| 2011/0137397 A1* | 6/2011 | Chau .................... A61F 2/2412 623/1.11 |
| 2011/0224785 A1* | 9/2011 | Hacohen ............... A61F 2/2418 623/2.18 |
| 2014/0222142 A1 | 8/2014 | Kovalsky et al. |
| 2014/0296969 A1* | 10/2014 | Tegels .................. A61F 2/2412 623/2.11 |
| 2015/0039081 A1 | 2/2015 | Costello |
| 2016/0038283 A1 | 2/2016 | Divekar et al. |
| 2016/0143730 A1 | 5/2016 | Kheradvar |
| 2018/0200049 A1 | 7/2018 | Chambers et al. |

\* cited by examiner 310
312

TRANSCATHETER HEART VALVE WITH PLICATION WINDOW AND TISSUE ANCHORS

CROSS-REFERENCE TO RELATED APPLICATIONS

Provided by Application Data Sheet per USPTO rules.

STATEMENT REGARDING FEDERALLY SPONSORED R&D

Provided by Application Data Sheet per with USPTO rules.

NAMES OF PARTIES TO JOINT RESEARCH AGREEMENT

Provided by Application Data Sheet per with USPTO rules.

REFERENCE TO SEQUENCE LISTING

Provided by Application Data Sheet per USPTO rules.

STATEMENT RE PRIOR DISCLOSURES

Provided by Application Data Sheet per USPTO rules.

BACKGROUND OF THE INVENTION

Field of the Invention

The invention relates to a transcatheter heart valve replacement (A61F2/2412), and in particular a device and method for percutaneous annular plication and heart valve deployment for mounting a pressure actuated flow control member as a replacement device for a heart valve, whereby the prosthesis has an atrial annular flange or cuff having one or more integral plication windows connected to a pressure actuated flow control member extending into the ventricle.

Description of the Related Art

The human heart has four chambers, two upper collection chambers are called atrium, and two lower pumping chambers called ventricles. The right-side atrium receives blood from the body and has a trapdoor opening, called a tricuspid valve, that delivers blood to the right-side ventricle. The right ventricle then pumps the blood a short distance, through a one-way valve called called a pulmonary valve, to the lungs where the blood is oxygenated. When the oxygenated blood is returned to the left side of the heart from the lungs, the blood reaches the left upper, collection chamber, called the left atrium. Here, the blood is released through a second trapdoor opening, called a mitral valve, into the large, muscular left ventricle, which pumps the blood at high pressure through a one-way valve called an aortic valve to return the oxygenated blood back to the body.

Heart valve disease, such as those caused by damage or a defect, can include stenosis and valvular insufficiency or regurgitation. Valvular stenosis causes the valve to become narrowed and hardened which can prevent blood flow to a downstream heart chamber or structure (e.g., aorta) to occur at the proper flow rate and cause the heart to work harder to pump the blood through the diseased valve. Diseased or damaged valves, which can be congenital, age-related, drug-induced, or caused by infection, can result in an enlarged, thickened heart that loses elasticity and efficiency.

Prosthetic heart valves have been developed for repair and replacement of diseased and/or damaged heart valves. Such valves can be percutaneously delivered and deployed at the site of the diseased heart valve through catheter-based systems. Such prosthetic heart valves can be delivered while in a low-profile or compressed/contracted arrangement so that the prosthetic valves can be contained within a sheath component of a delivery catheter and advanced through the patient's vasculature. Once positioned at the treatment site, the prosthetic valves can be expanded to engage tissue at the diseased heart valve region to, for instance, hold the prosthetic valve in position. While these prosthetic valves offer minimally invasive methods for heart valve repair and/or replacement, challenges remain to provide prosthetic valves that prevent leakage between the implanted prosthetic valve and the surrounding tissue (paravalvular leakage) and for preventing movement and/or migration of the prosthetic valve that could occur during the cardiac cycle.

For example, the repair or replacement of a valve can present numerous challenges due to differing anatomies and etiologies presented by individual patients, including varying sizes and topologies associated with an abnormal or unhealthy aortic valve that prevents proper alignment of the replacement (e.g., prosthetic) valve which can cause leakage, valve impingement or dislodgement of the prosthesis. Additionally, stenosis of a valve can deform the valvular area which can result in paravalvular leakage around an implanted replacement valve. Additional challenges can include providing a prosthetic valve that can be adjusted or repositioned during or after implantation and/or for replacing a previously implanted prosthetic valve.

In 1952 surgeons implanted the first mechanical heart valve. This first valve was a ball valve and it was designed by Dr. Charles Hufnagel. The recipient of this valve was a 30-year-old woman who could lead a normal life after the surgery. However, one downside of this design was that it could only be placed in the descending aorta instead of the heart itself. For this reason it did not fully correct the valve problem, only alleviate the symptoms. However it was a significant achievement because it proved that synthetic materials could be used to create heart valves.

In 1960, a new type of valve was invented and was successfully implanted. This valve is the Starr-Edwards ball valve, named after its originators. This valve was a modification of Hufnagel's original valve. The ball of the valve was slightly smaller and caged from both sides so it could be inserted into the heart itself.

The next development was tilting disc technology which was introduced in the late 1960s. These valves were a great improvement over the ball designs. The tilting dic technology allowed blood to flow in a more natural way while reducing damage to blood cells from mechanical forces. However, the struts of these valves tended to fracture from fatigue over time. As of 2003, more than 100,000 Omniscience and 300,000 Hall-Kaster/Medtronic-Hall tilting disc valves were implanted with essentially no mechanical failure.

In 1977, bi-leaflet heart valves were introduced by St. Jude. Similar to a native heart valve, blood flows directly through the center of the annulus of pyrolytic carbon valves mounted within nickel-titanium housing which makes these valves superior to other designs. However, a downside of this design is that it allows some regurgitation. A vast majority of mechanical heart valves used today have this design. As of 2003, more than 1.3 million St. Jude valves were deployed and over 500,000 Carbomedics valves with no failures to leaflets or housing. It should be noted that the human heart beats about 31 million times per year.

Development continues with compressible valves that are delivered via a catheter instead of requiring the trauma and complications of open heart surgery. This means that a cardiologist trained in endoscopy can, in theory, deploy a heart valve replacement during an outpatient procedure. However, transcatheter valves are often delivered by perforating the apex of the heart to access the ventricle, and the perforation is often used to anchor an annular valve replacement.

Additionally, a problem with stent-style replacement valves is that they often continue to have the regurgitation or leakage problems of prior generations of valves, as well as require expensive materials engineering in order to cope with the 100's of millions of cycles encountered during just a few years of normal heart function. Accordingly, there is still a need for alternative and simpler solutions to addressing valve-related heart pathologies.

BRIEF SUMMARY OF THE INVENTION

The invention provides advantages over prior designs. Specifically, the problems are addressed by providing a transcatheter delivered prosthetic valve having an asymmetric pericardial tissue covered wire frame with an upper angled collar of scalloped diamond-shapes forming an atrial flange, the atrial flange connected to a middle ring of longitudinally vertical diamond-shapes that is used to mount a reciprocating flow control conduit/tube, wherein the upper flange has a steep angle of inclination at the septal region, a shallower angle of inclination around the anterior and posterior annular regions, and an indent or cutout area near the coronary sinus region, wherein the septal region of the flange is contemplated as angled between 30-90 degrees to the horizontal plane of the annulus, and having a polyester material covering to promote tissue in-growth, and a non-leaflet containing reciprocating tube disposed with a lumen of the wire frame to reduce stenosis and calcification, and the an upper angled collar having from 1-8 plication windows, with 1-8 plication domes, each plication dome mountable over a plication window and having a plication tissue anchor mounted on the plication dome for engaging annular tissue through the plication window, and from 1-8 secondary tissue anchors, each secondary tissue anchor mounted on the wire frame for engaging annular tissue.

In some embodiments, there is a second lower angled collar of scalloped diamond shapes forming an sub-annular ventricular flange.

Accordingly, the present invention is directed to a transcatheter heart valve replacement comprising: an atrial sealing cuff frame having from 1-8 plication windows, said cuff frame connected to a collapsible flow control member that provides a reciprocating closable channel from a heart atrium to a heart ventricle, said cuff frame comprised of a braided or laser-cut wire frame having a substantially circular central aperture, said cuff frame partially covered with a biocompatible material, wherein each of said plication windows is an aperture within an outer region of the cuff frame between the central aperture and a circumferential edge of the cuff frame, said collapsible flow control member connected at an upper end to an inner perimeter of the central aperture of the cuff frame, and the collapsible flow control member extending beyond the central aperture of the cuff frame and having a lower end positioned with the ventricle of the heart, and from 1-8 plication domes, each plication dome mountable over a plication window and having a plication tissue anchor mounted on the plication dome for engaging annular tissue through the plication window, and from 1-8 secondary tissue anchors, each secondary tissue anchor mounted on the cuff frame for engaging annular tissue.

In another preferred embodiment, the invention comprises a transcatheter heart valve replacement as described and claimed herein, wherein the plication tissue anchor comprises a floating radio-opaque marker threaded onto the plication tissue anchor, wherein advancing the plication tissue anchor through tissue moves the floating radio-opaque marker from an initial distal lower thread position on the anchor to a secondary position on a higher thread.

In another preferred embodiment, the invention comprises a transcatheter heart valve replacement as described and claimed herein, wherein one or more of the plication tissue anchors or the secondary tissue anchors are selected from the group consisting of: a straight thread constant pitch fastener, a tapered thread constant pitch fastener, a straight thread variable pitch fastener, a tapered thread variable pitch fastener, and a sunken taper thread variable pitch fastener.

In another preferred embodiment, the invention comprises a transcatheter heart valve replacement as described and claimed herein, wherein the plication dome comprises an anchor ladder having steps or threads on the inner surface of the plication dome.

In another preferred embodiment, the invention comprises a transcatheter heart valve replacement as described and claimed herein, wherein the cuff frame is configured as a flat cone shape having a diameter R of 50-70 mm, a diameter r of 20-30 mm, and a height of 20-40 mm.

In another preferred embodiment, the invention comprises a transcatheter heart valve replacement as described and claimed herein, wherein the cuff frame has an inner wall and an outer wall, said inner wall having a biocompatible material comprising pericardial tissue, and said outer wall having a biocompatible material comprising a woven synthetic polyester material.

In another preferred embodiment, the invention comprises a transcatheter heart valve replacement as described and claimed herein, wherein the plication window is an uncovered aperture.

In another preferred embodiment, the invention comprises a transcatheter heart valve replacement as described and claimed herein, wherein the plication window is covered by either pericardial tissue or a woven synthetic polyester material.

In another preferred embodiment, the invention comprises a transcatheter heart valve replacement as described and claimed herein, wherein the cuff frame is configured as an hourglass flat conical shape having a top diameter R1 of 50-70 mm, a bottom diameter R2 of 50-70 mm, an internal diameter r of 20-30 mm, and a height of 20-50 mm.

In another preferred embodiment, the invention comprises a transcatheter heart valve replacement as described and claimed herein, wherein the collapsible flow control member has an internal diameter of 20-30 mm and a height of 30-80 mm, said member comprising three substantially flat rectangular panels of pericardial material joined to form a rounded triangular cylinder.

In another preferred embodiment, the invention comprises a transcatheter heart valve replacement as described and claimed herein, wherein the transcatheter heart valve replacement is compressible and fits when compressed within the internal diameter of a transcatheter implantation catheter having an internal diameter less than 22 Fr (7.33 mm) to 34 Fr (9.33 mm).

In another preferred embodiment, the invention comprises a transcatheter heart valve replacement as described and claimed herein, wherein the collapsible flow control member is supported with one or more longitudinal supports integrated into a fabric or material of the collapsible flow control member, the one or more longitudinal supports selected from rigid or semi-rigid ribs, rigid or semi-rigid battons, rigid or semi-rigid panels, and combination thereof.

In another preferred embodiment, the invention comprises a transcatheter heart valve replacement as described and claimed herein, wherein one or more of the plication tissue anchors or secondary tissue anchors are selected from the group consisting of: a helical coil, a screw, a dart, a pin, and a fastener means.

In another preferred embodiment, the invention comprises a method for securing a transcatheter heart valve prosthesis within a heart, the method comprising the steps: (i) advancing a procedure guide wire into a ventricle of a heart; (ii) advancing a 22 Fr-34 Fr steerable catheter over the procedure guide wire to deliver a compressed transcatheter heart valve prosthesis as described and claimed herein to an atrium of the ventricle of the heart; (iii) advancing the catheter to the valve annulus and releasing the self-expanding atrial sealing collar from within the catheter; (iv) advancing a plication dome over a dome guide wire to a plication window of the cuff frame; (v) anchoring a plication tissue anchor through the plication and into the annular tissue; and (vi) releasing said dome guide wire from attachment to the plication dome by actuating a release mechanism, and withdrawing the dome guide wire and steerable catheter from the heart.

BRIEF DESCRIPTION OF THE SEVERAL VIEWS OF DRAWING

FIG. 1 is an illustration of a top view of a heart valve prosthesis according to the present invention. FIG. 1 shows polyester mesh covering a valve frame encircling a collapsible flow control member and wherein the valve frame has meshless windows or tissue-capturing plication gaps.

FIG. 2(a)-(d) is an illustration of a plan view of a plication dome on a heart valve prosthesis according to the present invention. FIG. 2(a) shows a tissue anchor accessing annular tissue through the plication window. FIG. 2(b) shows the tissue anchor being actuated or rotated to advance into the annular tissue and raising the annular tissue up and through the plication window. FIG. 2(c) shows the tissue anchor completing the plication of the annular tissue into the plication window. FIG. 2(d) shows a cross-sectional view of the plicated annular tissue pulled into the plication window and dome using the plication tissue anchor. FIG. 2(d) shows how the annulus tissue is circumferentially foreshortened.

FIG. 3(a)-(c) is an illustration of a plan view of a tissue anchor having a floating radio-opaque marker. FIG. 3(a) shows the tissue anchor accessing the annular tissue with the radio-opaque marker at the distal end of the anchor and in contact with the atrial surface of the annular tissue. FIG. 3(b) shows the tissue anchor advancing into the annular tissue with the radio-opaque marker threaded onto the tissue anchor and maintaining position on the atrial surface of the annular tissue. FIG. 3(c) shows the tissue anchor completely advanced into the annular tissue such that the tissue anchor and the threaded floating marker are now adjacent, indicating the desired depth, tension, and/or plication of the tissue anchor with respect to the annular tissue.

Figure 8A:
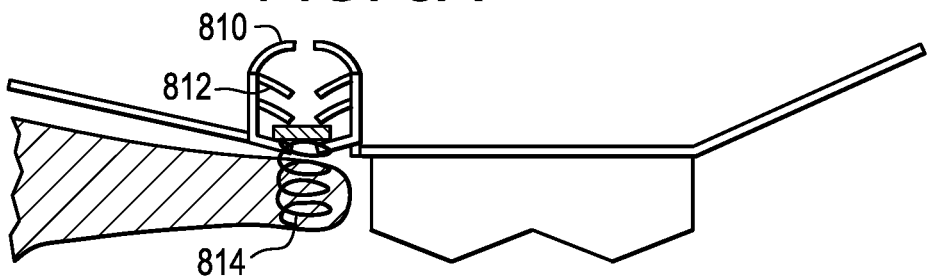
Figure 8B:
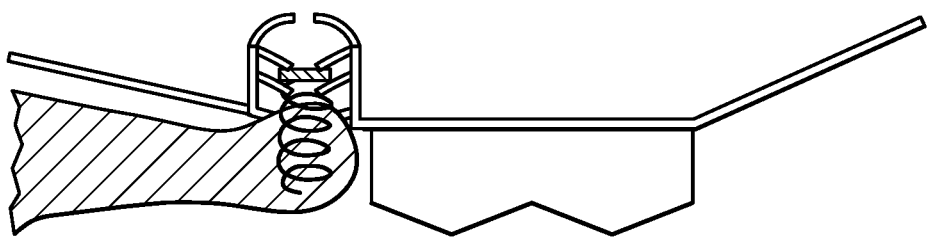
Figure 8C:
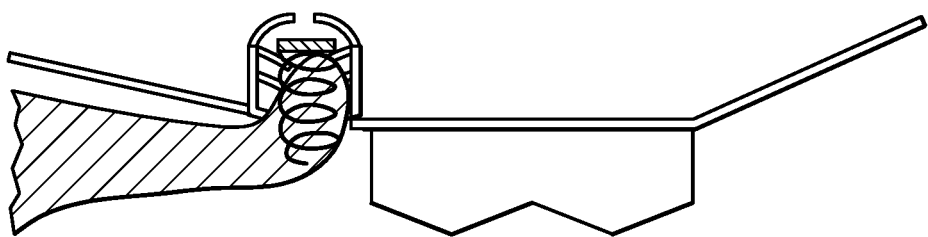
Figure 8D:
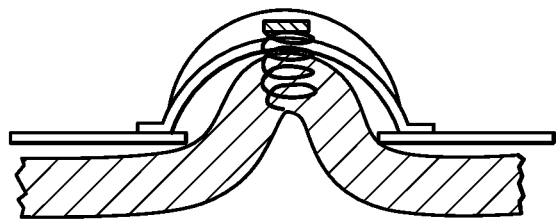

FIG. 8(a)-(d) is an illustration of a plan view of heart valve prosthesis according to the invention having a laddered plication dome. FIG. 8(a) shows a tissue anchor accessing annular tissue through a plication window in the cuff frame with the head of the tissue anchor engaged in a lower rung of an anchor ladder. FIG. 8(b) shows a tissue anchor accessing annular tissue through a plication window in the cuff frame with the head of the tissue anchor advancing up the anchor ladder and engaged in a middle rung of the anchor ladder. FIG. 8(c) shows a tissue anchor accessing annular tissue through a plication window in the cuff frame with the head of the tissue anchor advancing up the anchor ladder and engaged in a top rung of an anchor ladder. FIG. 8(d) shows a cross-sectional view of the plicated annular tissue pulled into the plication window and dome using the plication tissue anchor. FIG. 8(d) shows how the annulus tissue is circumferentially foreshortened.

Figure 9:
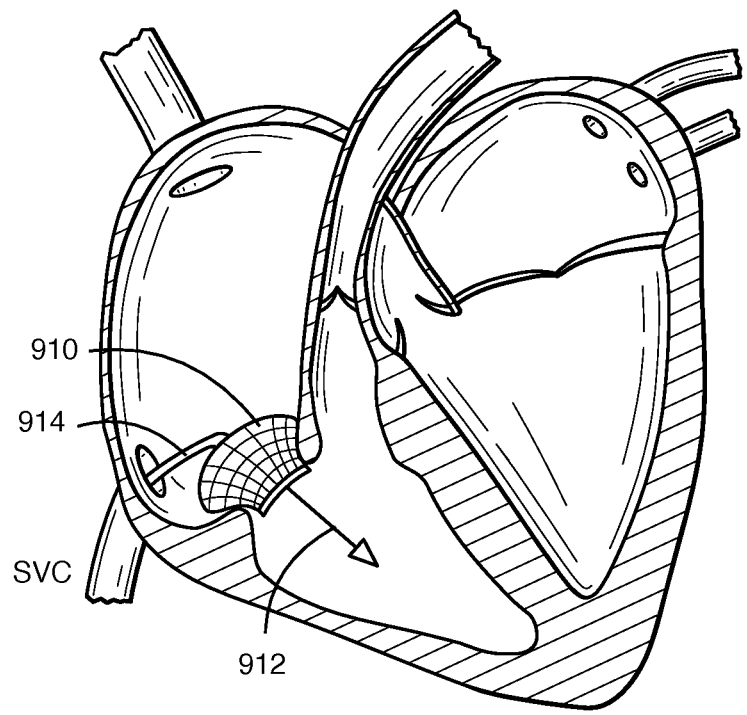

FIG. 9 is an illustration of a plan view of catheter deployment through the inferior vena cava of a heart valve prosthesis according to the present invention. FIG. 9 shows guide wire advanced in the right ventricle with the heart valve prosthesis being ejected from the distal end of the catheter.

Figure 10:
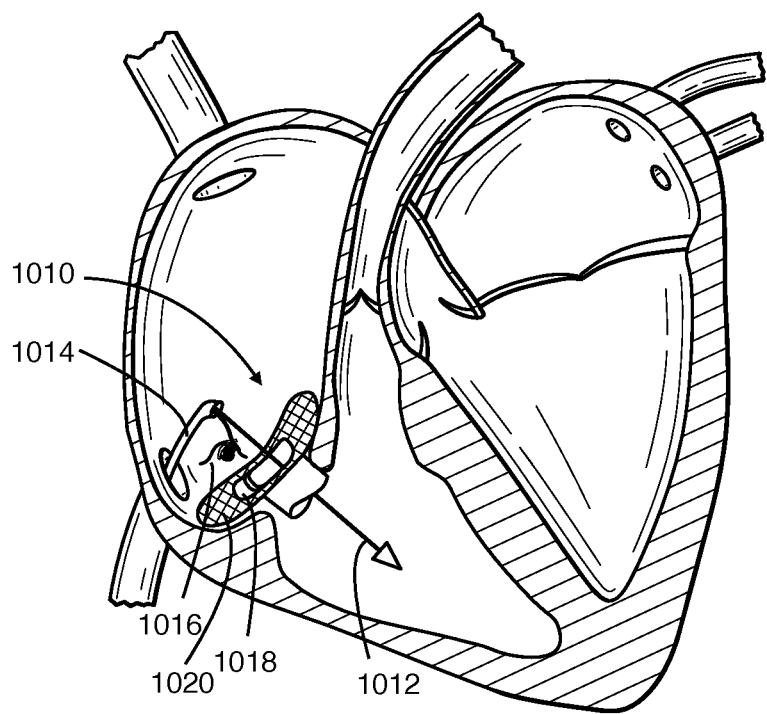

FIG. 10 is an illustration of a plan view of catheter deployment through the inferior vena cava of a heart valve prosthesis according to the present invention. FIG. 10 shows guide wire advanced in the right ventricle with the heart valve prosthesis deployed in the tricuspid annulus, and a plication dome is advanced from the distal end of the catheter towards a plication window in the cuff/flange.

Figure 11A:
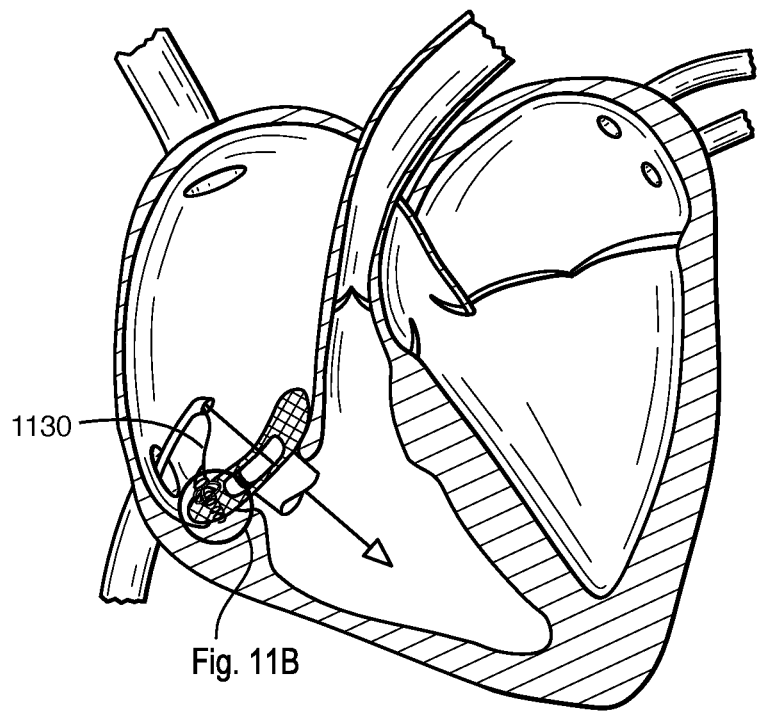
Figure 11B:
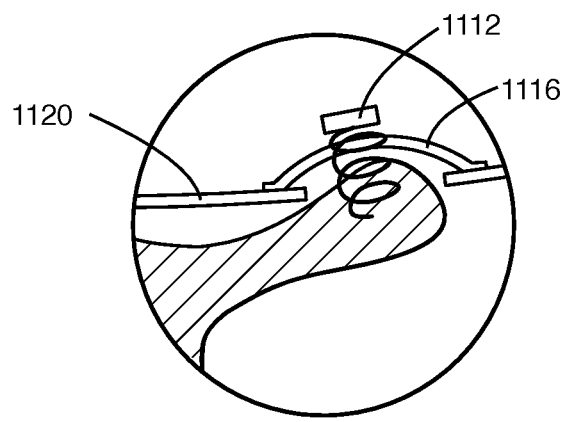

FIG. 11(a)-(b) is an illustration of a plan view of catheter deployment through the inferior vena cava of a heart valve prosthesis according to the present invention. FIG. 11(a) shows guide wire advanced in the right ventricle with the heart valve prosthesis deployed in the tricuspid annulus, and a plication dome is mounted on a plication window in the cuff/flange, with inset showing tissue anchor advancing into the atrial surface of the annular tissue. FIG. 11(b) shows a close-up detail view of a plication dome over a valve atrial cuff with a tissue anchor inserted into native annular tissue.

Figure 12:
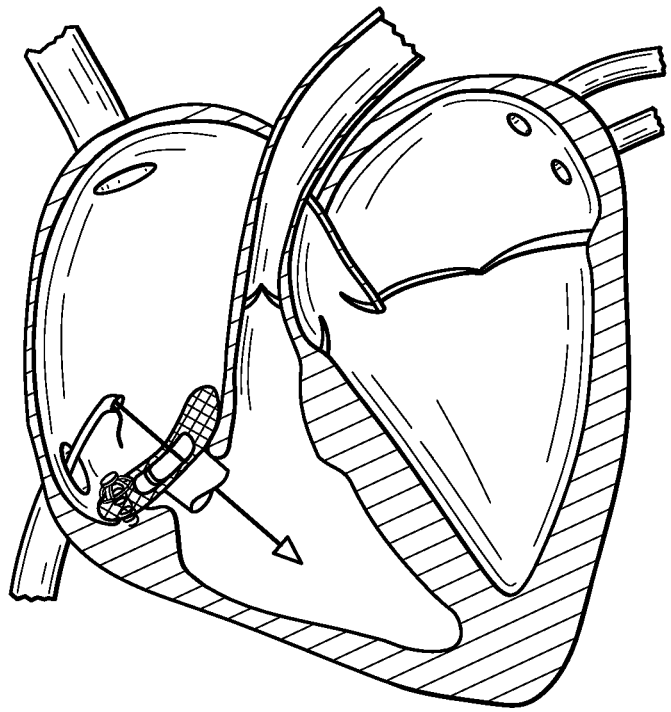

FIG. 12 is an illustration of a plan view of catheter deployment through the inferior vena cava of a heart valve prosthesis according to the present invention. FIG. 12 shows the control wire for the plication dome being withdrawn and the plication dome mounted on a plication window in the cuff/flange, with tissue anchor advanced into the atrial surface of the annular tissue.

Figure 13:
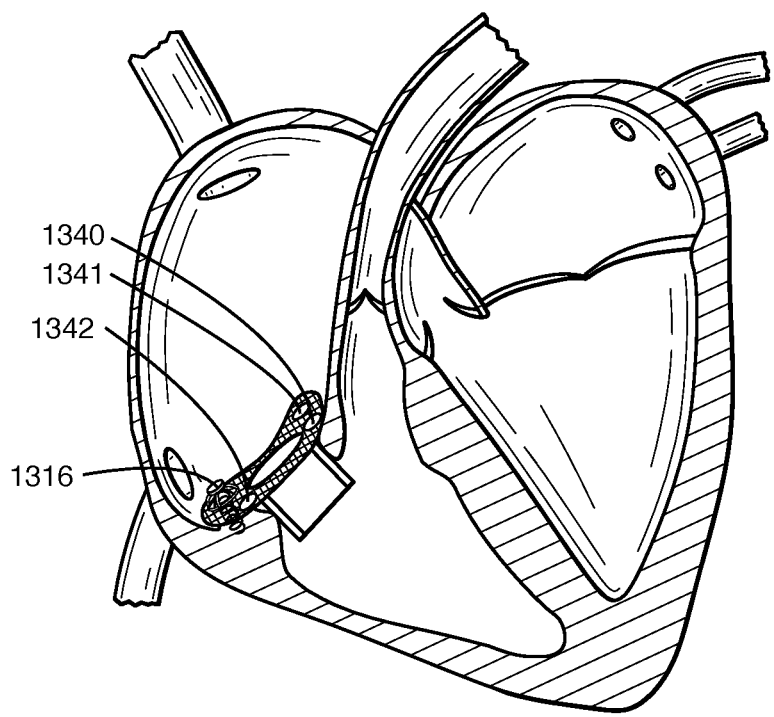

FIG. 13 is an illustration of a perspective view of a heart valve prosthesis according to the present invention deployed within the tricuspid annulus. FIG. 13 shows a plication dome and 3 topologically diverse tissue anchors mounting the heart valve prosthesis to the annular tissue.

Figure 14:
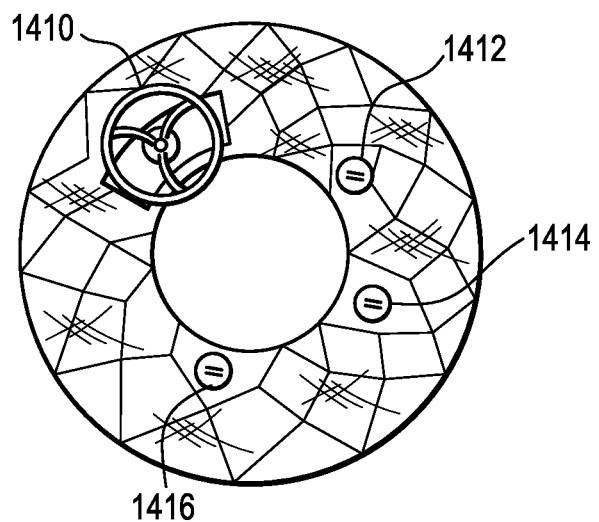

FIG. 14 is an illustration of a top view of a heart valve prosthesis according to the present invention deployed within the tricuspid annulus. FIG. 14 shows a plication dome and 3 topologically diverse tissue anchors mounting the heart valve prosthesis to the annular tissue.

Figure 15:
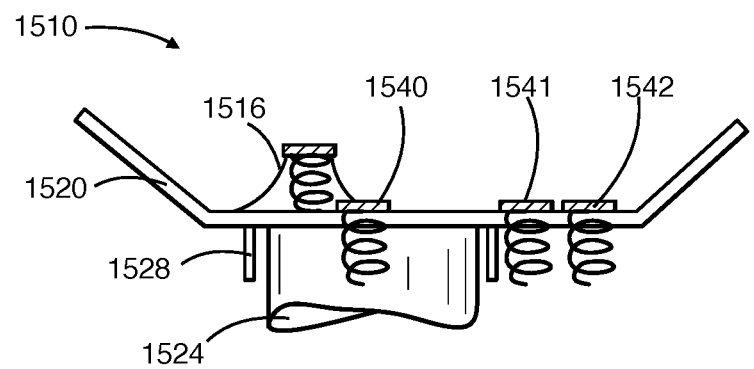

FIG. 15 is an illustration of a plan view of a heart valve prosthesis according to the present invention. FIG. 15 shows a plication dome and 3 topologically diverse tissue anchors mounting the heart valve prosthesis to the annular tissue.

Figure 16:
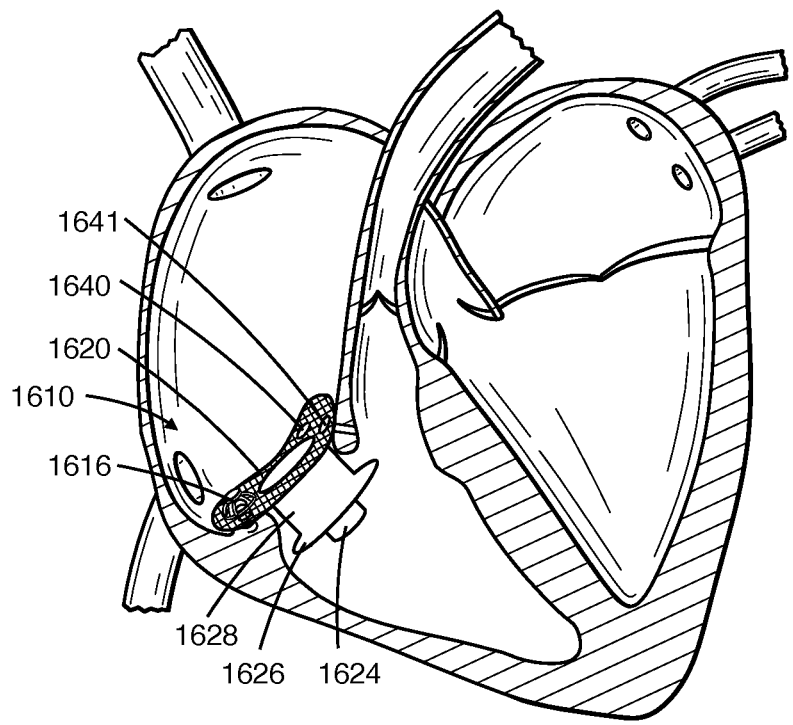

FIG. 16 is an illustration of a perspective view of a heart valve prosthesis according to the present invention deployed within the tricuspid annulus. FIG. 16 shows a plication dome and 2 topologically diverse tissue anchors mounting the heart valve prosthesis to the annular tissue.

Figure 17:
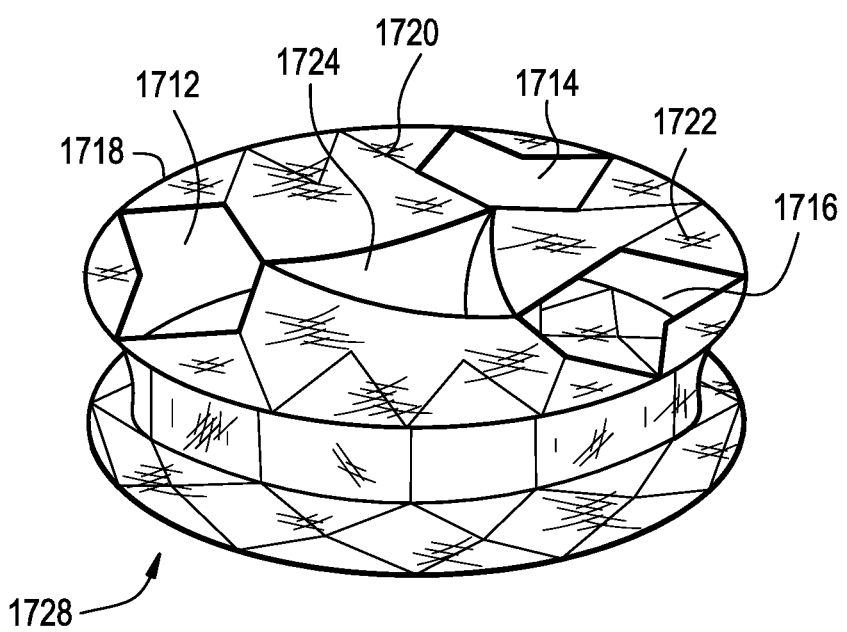

FIG. 17 is an illustration of a perspective view of a heart valve prosthesis according to the present invention having a upper cuff with three uncovered plication windows and a central aperture having the collapsible flow control member (FCM) disposed therein and providing an axial tube valve.

DETAILED DESCRIPTION OF THE INVENTION

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Rather, these embodiments are provided so that this disclosure will be thorough and complete, and will fully convey the scope of the invention to those skilled in the art. Like numbers refer to like elements throughout. As used herein the term "and/or" includes any and all combinations of one or more of the associated listed items.

The terminology used herein is for the purpose of describing particular embodiments only and is not intended to limit the full scope of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal subparts. As will be understood by one skilled in the art, a range includes each individual member.

DEFINITIONS

Transcatheter

In the description and claims herein, the term "transcatheter" is used to define the process of accessing, controlling, and delivering a medical device or instrument within the lumen of a catheter that is deployed into a heart chamber, as well as an item that has been delivered or controlled by such as process. Transcatheter access is known to include via femoral artery and femoral vein, via brachial artery and vein, via carotid and jugular, via intercostal (rib) space, and via sub-xyphoid.

Wire Frame or Flange or Collar

In the description and claims herein, the terms "frame" or "flange or "collar" refers to flange, disk, band, ring, hem, rim, or belt that is a substantially flat cone shaped braided or laser-cut wire frame covered with a biocompatible material and having a central aperture. An atrial frame or collar is located in the atrium on the atrial floor and is used to direct blood into the flow control member attached to the aperture and seal against blood leakage around the flow control member. A ventricular frame or collar is located in the ventricle immediately below the native annulus and is used to prevent regurgitant leakage during systole, to prevent dislodging of the device during systole, to sandwich or compress the native annulus or adjacent tissue against the atrial collar, and to attach to a mid-section of the flow control member/conduit. The frames may be formed from braided or laser-cut Nitinol and as such may be compressed for transcatheter delivery and may be expandable as a self-expandable shape memory element or using a transcatheter expansion balloon. Some embodiments may have both an atrial collar and a ventricular collar, whereas other embodiments within the scope of the invention include prosthetic valves having either a single atrial collar or a single ventricular collar.

Flow Control Member

In the description and claims herein, the term "collapsible flow control member" refers to a tube or conduit having flexible material that is open to blood flowing during diastole from atrium to ventricle, and that closes from systolic ventricular pressure applied to the outer surface. Repeated opening and closing in sequence can be described as "reciprocating".

Tissue Anchor

In the description and claims herein, the term "tissue anchor" or "plication tissue anchor" or "secondary tissue anchor", or "dart" or "pin" refers to a fastening device that connects the upper atrial frame to the the native annular tissue, usually at or near the periphery of the collar. The anchor may be positioned to avoid piercing tissue and just rely on the compressive force of the two plate-like collars on the captured tissue, or the anchor, itself or with an integrated securement wire, may pierce through native tissue to provide anchoring, or a combination of both. The anchor may have a specialized securement mechanism, such as a pointed tip with a groove and flanged shoulder that is inserted or popped into a mated aperture or an array of mated apertures that allow the anchor to attach, but prevent detachment when the aperture periphery locks into the groove near the flanged shoulder. The securement wire may be attached or anchored to the collar opposite the pin by any attachment or anchoring mechanisms, including a knot, a suture, a wire crimp, a wire lock having a cam mechanism, or combinations.

Support Post

The term "support post" refers to a rigid or semi-rigid length of material such as Nitinol or PEEK, that may be mounted on a spoked frame and that runs axially, or down the center of, or within a sewn seam of—, the flexible flow control member. The flow control member may be unattached to the support post, or the flow control member may be directly or indirectly attached to the support post.

In the description that follows, the term "body channel" is used to define a blood conduit or vessel within the body. Of course, the particular application of the prosthetic heart valve determines the body channel at issue. An aortic valve replacement, for example, would be implanted in, or adjacent to, the aortic annulus. Likewise, a tricuspid or mitral valve replacement will be implanted at the tricuspid or mitral annulus. Certain features of the present invention are particularly advantageous for one implantation site or the other. However, unless the combination is structurally impossible, or excluded by claim language, any of the heart valve embodiments described herein could be implanted in any body channel.

The term "lumen" refers to the inside of the cylinder tube. The term "bore" refers to the inner diameter.

Displacement—The Volume of Fluid Displaced by One Complete Stroke or Revolution

Ejection fraction is a measurement of the percentage of blood leaving your heart each time it contracts. During each heartbeat pumping cycle, the heart contracts and relaxes. When your heart contracts, it ejects blood from the two pumping chambers (ventricles)

As a point of further definition, the term "expandable" is used herein to refer to a component of the heart valve capable of expanding from a first, delivery diameter to a second, implantation diameter. An expandable structure, therefore, does not mean one that might undergo slight expansion from a rise in temperature, or other such incidental cause. Conversely, "non-expandable" should not be interpreted to mean completely rigid or a dimensionally stable, as some slight expansion of conventional "non-expandable" heart valves, for example, may be observed.

Force—A push or pull acting upon a body. In a hydraulic cylinder, it is the product of the pressure on the fluid, multiplied by the effective area of the cylinder piston.

Prosthetic Valve

The term prosthesis or prosthetic encompasses both complete replacement of an anatomical part, e.g. a new mechanical valve replaces a native valve, as well as medical devices that take the place of and/or assist, repair, or improve existing anatomical parts, e.g. native valve is left in place. For mounting within a passive assist cage, the invention contemplates a wide variety of (bio)prosthetic artificial heart valves. Contemplated as within the scope of the invention are ball valves (e.g. Starr-Edwards), bileaflet valves (St. Jude), tilting disc valves (e.g. Bjork-Shiley), stented pericardium heart-valve prosthesis' (bovine, porcine, ovine) (Edwards line of bioprostheses, St. Jude prosthetic valves), as well as homograft and autograft valves. For bioprosthetic pericardial valves, it is contemplated to use bioprosthetic aortic valves, bioprosthetic mitral valves, bioprosthetic tricuspid valves, and bioprosthetic pulmonary valves.

The terms "distal" and "proximal" are used in the following description with respect to a position or direction relative to the treating clinician or with respect to a prosthetic heart valve device. For example, "distal" or "distally" are a position distant from or in a direction away from the clinician when referring to delivery procedures or along a vasculature. Likewise, "proximal" and "proximally" are a position near or in a direction toward the clinician. With respect to a prosthetic heart valve device, the terms "proximal" and "distal" can refer to the location of portions of the device with respect to the direction of blood flow. For example, proximal can refer to an upstream position or a position of blood inflow, and distal can refer to a downstream position or a position of blood outflow.

Frame Material

Preferably, the frame is made from superelastic metal wire, such as Nitinol™ wire or other similarly functioning material. The material may be used for the frame/stent, for the collar, and/or for anchors. It is contemplated as within the scope of the invention to use other shape memory alloys such as Cu—Zn—Al—Ni alloys, Cu—Al—Ni alloys, as well as polymer composites including composites containing carbon nanotubes, carbon fibers, metal fibers, glass fibers, and polymer fibers.

It is contemplated that the frame may be constructed as a braided wire frame or as a laser cut wire frame. Such materials are available from any number of commercial manufacturers, such as Pulse Systems. Laser cut wire frames are preferably made from Nickel-Titanium (Nitinol™), but also without limitation made from stainless steel, cobalt chromium, titanium, and other functionally equivalent metals and alloys, or Pulse Systems braided frame that is shape-set by heat treating on a fixture or mandrel.

One key aspect of the frame design is that it be compressible and when released have the stated property that it return to its original (uncompressed) shape. This requirement limits the potential material selections to metals and plastics that have shape memory properties. With regards to metals, Nitinol has been found to be especially useful since it can be processed to be austhenitic, martensitic or super elastic. Martensitic and super elastic alloys can be processed to demonstrate the required compression features.

The frame may be made from stainless steel, a pseudoelastic metal such as nickel titanium alloy or NITINOL™, or a so-called super alloy, which may have a base metal of nickel, cobalt, chromium, or other metal. It is also understood that the frame/wire may comprise various materials other than Nitinol that have elastic and/or memory properties, such as spring stainless steel, trade named alloys such as ELGILOY™, HASTELLOY™, CoCrNi alloys (e.g., trade name PHYNOX), MP35N™, CoCrMo alloys, or a mixture of metal and polymer fibers. Depending on the individual material selected, strand diameter, number of strands, and pitch may be altered to achieve the desired properties of frame.

Frame Structure

In one embodiment, the frame is a flexible metal frame or support structure having a plurality of ribs and/or struts geometrically arranged to provide a latticework capable of being radially compressed for delivery to a target native valve site, and capable of radially expanding for deployment and implantation at the target native valve site. The struts can be arranged in a plurality of geometrical patterns that can expand or flex and contract while providing sufficient resilience and strength for maintaining position of the prosthetic with respect to the native anatomy of the heart. For example, the struts can be arranged in a circumferential pattern about the longitudinal axis, wherein the circumferential pattern includes a series of diamond, zig-zagged, sinusoidal, or other geometric shapes.

In one preferred embodiment, the frame has an upper angled collar of scalloped diamond-shapes forming the atrial flange, with a middle ring of longitudinally vertical diamond-shapes for mounting the reciprocating flow control member. In some embodiments, there is a second lower angled collar of scalloped diamond shapes forming an sub-annular ventricular flange.

In some embodiments described herein, and in order to transform or self-expand between an initial compressed configuration and the deployed configuration, the frame is formed from a resilient or shape memory material, such as a nickel titanium alloy such as e.g., NITINOL™, developed by the U.S. Navy Ordinance Lab (Ni-Ti-N.O.L.), that has a mechanical memory to return to the deployed or expanded configuration.

In one embodiment, the frame has a unitary structure that defines a conical structure having a single atrial flange or a spool-shaped structure having both an atrial and a ventricular flange, and to which a flexible sheet of pericardium covers one side, a DACRON™ or similar polyethylene material covers the other side, and reciprocating flow control member is mounted within the lumen of the valve frame.

Asymmetric Frame

In one preferred embodiment, the frame is asymmetric wherein the upper flange has a steep angle of inclination at the septal region, a shallower angle of inclination around the anterior and posterior annular regions, and an indent or cutout area near the coronary sinus region. The septal region of the flange is contemplated as angled between 30-90 degrees to the horizontal plane of the annulus or the horizontal plane perpendicular to the longitudinal axis down the lumen of the valve in order to accommodate the native septal annulus and adjacent tissue, which has a steeper vertical inclination compared to other regions of the native annulus.

This septal accommodation is an important aspect of the invention since the septal annulus region is known that have important electrical cardiac tissue, the Triangle of Koch, which is somewhat of a no-fly zone, in the field of prosthetic valves and valve repair, since damage of this region can cause significant damage to the electrical conductivity of the heart necessary for its functioning.

The inventive prosthesis herein provides a septal sealing and in-growth without requiring traumatic tissue anchoring in the delicate septal annulus region. By providing transcatheter delivery, traumatic open-heart and percutaneous puncture is avoided. By providing a covered sealing flange, PVL sealing is provided. By using a polyester material covering, septal region in-growth is promoted and achieved. By using non-septal region tissue anchors through an simple Nitinol frame, deployment is simplified and dislodgement is avoided.

The frame can be formed as a unitary structure, for example, from a laser cut, fenestrated, NITINOL™ or other metal tube. Mechanical memory may be imparted to the structure that forms the frame by thermal treatment to achieve a spring temper in the stainless steel, for example, or to set a shape memory in a susceptible metal alloy, such as NITINOL™. The frame may also include polymers or combinations of metals, polymers or other materials. In an alternative embodiment, the frame can be a balloon-expandable tubular metal stent.

In other embodiments, the frame can include separately manufactured components that are coupled, linked, welded, or otherwise mechanically attached to one another to form the frame. For example, attachment posts can be coupled at or near the struts as defined by a diamond-shaped geometry of the frame.

In particular embodiments, the frame may be assembled and coupled by a variety of methods known in the art, e.g., soldering, welding, bonding, rivets or other fasteners, mechanical interlocking, or any combination thereof.

Frame Manufacture—Laser Cut

One possible construction of the wire frame envisions the laser cutting of a thin, isodiametric Nitinol tube. The laser cuts form regular cutouts in the thin Nitinol tube.

Secondarily the tube is placed on a mold of the desired shape, heated to the Martensitic temperature and quenched. The treatment of the wire frame in this manner will form a device that has shape memory properties and will readily revert to the memory shape at the calibrated temperature.

Frame Manufacture—Braided Wire

A frame can be constructed utilizing simple braiding techniques. Using a Nitinol wire—for example a 0.012" wire—and a simple braiding fixture, the wire is wound on the braiding fixture in a simple over/under braiding pattern until an isodiametric tube is formed from a single wire. The two loose ends of the wire are coupled using a stainless steel or Nitinol coupling tube into which the loose ends are placed and crimped. Angular braids of approximately 60 degrees have been found to be particularly useful. Secondarily, the braided wire frame is placed on a shaping fixture and placed in a muffle furnace at a specified temperature to set the wire frame to the desired shape and to develop the martensitic or super elastic properties desired.

Tethers

The tethers are made from surgical-grade materials such as biocompatible polymer suture material. Non-limiting examples of such material include ultra high-molecular weight polyethylene (UHMWPE), 2-0 exPFTE (polytetrafluoroethylene) or 2-0 polypropylene. In one embodiment the tethers are inelastic. It is also contemplated that one or more of the tethers may optionally be elastic to provide an even further degree of compliance of the valve during the cardiac cycle.

Tines—Anchors—Tines/Barbs

The device can be seated within the valvular annulus through the use of tines or barbs. These may be used in conjunction with, or in place of one or more tethers. The tines or barbs are located to provide attachment to adjacent tissue. Tines are forced into the annular tissue by mechanical means such as using a balloon catheter. In one non-limiting embodiment, the tines may optionally be semi-circular hooks that upon expansion of the wire frame body, pierce, rotate into, and hold annular tissue securely. Anchors are deployed by over-wire delivery of an anchor or anchors through a delivery catheter. The catheter may have multiple axial lumens for delivery of a variety of anchoring tools, including anchor setting tools, force application tools, hooks, snaring tools, cutting tools, radio-frequency and radiological visualization tools and markers, and suture/thread manipulation tools. Once the anchor(s) are attached to the moderator band, tensioning tools may be used to adjust the length of tethers that connect to an implanted valve to adjust and secure the implant as necessary for proper functioning. It is also contemplated that anchors may be spring-loaded and may have tether-attachment or tether-capture mechanisms built into the tethering face of the anchor(s). Anchors may also have in-growth material, such as polyester fibers, to promote in-growth of the anchors into the myocardium.

In one embodiment, where a prosthetic valve may or may not include a ventricular collar, the anchor or dart is not attached to a lower ventricular collar, but is attached directly into annular tissue or other tissue useful for anchoring.

Tube and/or Cover Material—Biological Tissue—

The tissue used herein is a biological tissue that is a chemically stabilized pericardial tissue of an animal, such as a cow (bovine pericardium) or sheep (ovine pericardium) or pig (porcine pericardium) or horse (equine pericardium). Preferably, the tissue is bovine pericardial tissue. Examples of suitable tissue include that used in the products Dura-guard®, Peri-Guard®, and Vascu-Guard®, all products currently used in surgical procedures, and which are marketed as being harvested generally from cattle less than 30 months old. Other patents and publications disclose the surgical use of harvested, biocompatible animal thin tissues suitable herein as biocompatible "jackets" or sleeves for implantable stents, including for example, U.S. Pat. No. 5,554,185 to Block, U.S. Pat. No. 7,108,717 to Design & Performance-Cyprus Limited disclosing a covered stent assembly, U.S. Pat. No. 6,440,164 to Scimed Life Systems, Inc. disclosing a bioprosthetic valve for implantation, and U.S. Pat. No. 5,336,616 to LifeCell Corporation discloses acellular collagen-based tissue matrix for transplantation.

Polymers

In one preferred embodiment, the conduit may optionally be made from a synthetic material such a polyurethane or polytetrafluoroethylene.

Where a thin, durable synthetic material is contemplated, e.g. for a covering, synthetic polymer materials such expanded polytetrafluoroethylene or polyester may optionally be used. Other suitable materials may optionally include thermoplastic polycarbonate urethane, polyether urethane, segmented polyether urethane, silicone polyether urethane, silicone-polycarbonate urethane, and ultra-high molecular weight polyethylene. Additional biocompatible polymers may optionally include polyolefins, elastomers, polyethylene-glycols, polyethersulphones, polysulphones, polyvinylpyrrolidones, polyvinylchlorides, other fluoropolymers, silicone polyesters, siloxane polymers and/or oligomers, and/or polylactones, and block co-polymers using the same.

Polyamides (PA)

PA is an early engineering thermoplastic invented that consists of a "super polyester" fiber with molecular weight greater than 10,000. It is commonly called Nylon. Application of polyamides includes transparent tubing's for cardiovascular applications, hemodialysis membranes, and also production of percutaneous transluminal coronary angioplasty (PTCA) catheters.

Polyolefin

Polyolefins include polyethylene and polypropylene are the two important polymers of polyolefins and have better biocompatibility and chemical resistance. In cardiovascular uses, both low-density polyethylene and high-density polyethylene are utilized in making tubing and housings. Polypropylene is used for making heart valve structures.

Polyesters

Polyesters includes polyethylene-terephthalate (PET), using the name Dacron. It is typically used as knitted or woven fabric for vascular grafts. Woven PET has smaller pores which reduces blood leakage and better efficiency as vascular grafts compared with the knitted one. PET grafts are also available with a protein coating (collagen or albumin) for reducing blood loss and better biocompatibility [39]. PET vascular grafts with endothelial cells have been searched as a means for improving patency rates. Moreover, polyesters are widely preferred material for the manufacturing of bioabsorbable stents. Poly-L-lactic acids (PLLA), polyglycolic acid (PGA), and poly(D, L-lactide/glycolide) copolymer (PDLA) are some of the commonly used bioabsorbable polymers.

Polytetrafluoroethylene

Polytetrafluoroethylene (PTFE) is synthetic fluorocarbon polymer with the common commercial name of Teflon by Dupont Co. Common applications of PTFE in cardiovascular engineering include vascular grafts and heart valves. PTFE sutures are used in the repair of mitral valve for myxomatous disease and also in surgery for prolapse of the anterior or posterior leaflets of mitral valves. PTFE is particularly used in implantable prosthetic heart valve rings. It has been successfully used as vascular grafts when the devices are implanted in high-flow, large-diameter arteries such as the aorta. Problem occurs when it is implanted below aortic bifurcations and another form of PTFE called elongated-PTFE (e-PTFE) was explored. Expanded PTFE is formed by compression of PTFE in the presence of career medium and finally extruding the mixture. Extrudate formed by this process is then heated to near its glass transition temperature and stretched to obtain microscopically porous PTFE known as e-PTFE. This form of PTFE was indicated for use in smaller arteries with lower flow rates promoting low thrombogenicity, lower rates of restenosis and hemostasis, less calcification, and biochemically inert properties.

Polyurethanes

Polyurethane has good physiochemical and mechanical properties and is highly biocompatible which allows unrestricted usage in blood contacting devices. It has high shear strength, elasticity, and transparency. Moreover, the surface of polyurethane has good resistance for microbes and the thrombosis formation by PU is almost similar to the versatile cardiovascular biomaterial like PTFE. Conventionally, segmented polyurethanes (SPUs) have been used for various cardiovascular applications such as valve structures, pacemaker leads and ventricular assisting device.

Covered Wire Frame Materials

Drug-eluting wire frames are contemplated for use herein. DES basically consist of three parts: wire frame platform, coating, and drug. Some of the examples for polymer free DES are Amazon Pax (MINVASYS) using Amazonia CroCo (L605) cobalt chromium (Co—Cr) wire frame with Paclitaxel as an antiproliferative agent and abluminal coating have been utilized as the carrier of the drug. BioFreedom (Biosensors Inc.) using stainless steel as base with modified abluminal coating as carrier surface for the antiproliferative drug Biolimus A9. Optima (CID S.r.l.) using 316 L stainless steel wire frame as base for the drug Tacrolimus and utilizing integrated turbostratic carbofilm as the drug carrier. VESTA sync (MIV Therapeutics) using GenX stainless steel (316 L) as base utilizing microporous hydroxyapatite coating as carrier for the drug Sirolimus. YUKON choice (Translumina) used 316 L stainless steel as base for the drugs Sirolimus in combination with Probucol.

Biosorbable polymers may also be used herein as a carrier matrix for drugs. Cypher, Taxus, and Endeavour are the three basic type of bioabsorbable DES. Cypher (J&J, Cordis) uses a 316 L stainless steel coated with polyethylene vinyl acetate (PEVA) and poly-butyl methacrylate (PBMA) for carrying the drug Sirolimus. Taxus (Boston Scientific) utilizes 316 L stainless steel wire frames coated with translute Styrene Isoprene Butadiene (SIBS) copolymer for carrying Paclitaxel which elutes over a period of about 90 days. Endeavour (Medtronic) uses a cobalt chrome driver wire frame for carrying zotarolimus with phosphorylcholine as drug carrier. BioMatrix employing S-Wire frame (316 L) stainless steel as base with polylactic acid surface for carrying the antiproliferative drug Biolimus. ELIXIR-DES program (Elixir Medical Corp) consisting both polyester and polylactide coated wire frames for carrying the drug novolimus with cobalt-chromium (Co—Cr) as base. JACTAX (Boston Scientific Corp.) utilized D-lactic polylactic acid (DLPLA) coated (316 L) stainless steel wire frames for carrying Paclitaxel. NEVO (Cordis Corporation, Johnson & Johnson) used cobalt chromium (Co—Cr) wire frame coated with polylactic-co-glycolic acid (PLGA) for carrying the drug Sirolimus.

Examples of preferred embodiments of the reciprocating pressure conduit valve include the following details and features.

Example—General

Provided herein are systems, devices and methods suitable for percutaneous delivery and implantation of a prosthetic heart valve having a reciprocating pressure conduit valve in a heart of a patient. In some embodiments, methods and devices are presented for the treatment of valve disease by minimally invasive implantation of artificial or prosthetic heart valves. For example, a prosthetic heart valve device, in accordance with embodiments described herein, can be implanted for replacement of a diseased or damaged native valve or prior implanted prosthetic valve in a patient, such as in a patient suffering from valve stenosis. In further embodiments, the device is suitable for implantation and replacement of other diseased or damaged heart valves, including the tricuspid, pulmonary, aortic, and mitral heart valves.

In this example, a heart valve prosthesis in a radially expanded or deployed configuration (e.g., a deployed state) includes a frame or expandable structural support that includes a generally cylindrically-shaped structure that provides a mounting structure for a reciprocating pressure conduit valve that defines a lumen through which blood can flow.

Example—Sleeve/Conduit/Tube

One preferred embodiment of a tethered transcatheter valve is a heart valve substitute or successor comprising a pliant tubular conduit that is mounted on a resilient annular or ventricular frame, wherein the pliant tubular conduit is a reciprocating mechanical member that is actuated by pressurized working fluid, blood, within the ventricle during systole, and wherein the frame includes openings or plication windows for capturing and anchoring annular tissue with tissue anchors. Importantly, this heart valve substitute does not have a traditional valve configuration. Additionally, the device can be delivered to the ventricle compressed within a catheter, and expelled from the catheter to be deployed without open heart surgery.

Example—Valve

In another preferred embodiment of a transcatheter valve, comprises: (i) a atrial sealing frame and wherein the atrial frame includes openings or plication windows for capturing and anchoring annular tissue with tissue anchors, and (ii) a ventricular sealing collar/flange/frame, each of said atrial and ventricular frame connected to (iii) a collapsible flow control member that provides a reciprocating closable channel from a heart atrium to a heart ventricle, each of said frames comprised of a pair of flat conical shaped braided or laser-cut wire frame covered with a biocompatible material and each having a central aperture, the collapsible flow control member connected at an upper end to an inner perimeter of the central aperture of the atrial sealing frame, the collapsible flow control member connected at a middle section to an inner perimeter of the central aperture of the ventricular sealing frame, and the collapsible flow control member optionally extending beyond the central aperture of the ventricular sealing frame and having a lower end positioned with the ventricle of the heart, and (iv) from 2-12 tissue anchors, wherein the collapsible flow control member defines a channel therein, said channel having a volume that ranges from 1.57 mL-18.84 mL, said member having an average radius of 4.0-16.5 mm and an average height of 20-60 mm, said member comprised of decellularized pericardium or polymer, said member having top end, a bottom end, an internal surface, and an external surface, said member is compressible under a pressure of 50-160 mm Hg on the external surface to close the channel, and said member is expandable under a pressure of 40-80 mm Hg on the internal surface to open the channel, the collars have an average side length of 5-20 mm, an aperture having an average expanded diameter of 30-35 mm, and a perimeter having an average expanded diameter/circumference of 40-60 mm, said collars having a cover; and and optional one-piece rigid or semi-rigid axial post disposed with the lumen of the sleeve to support the length-wise integrity of the flexible member.

Example—Flow Control Member

In another preferred embodiment of a transcatheter valve, there is provided a feature wherein the flow control member is shaped as a conic cylinder, said top end having a diameter of 30-35 mm and said bottom end having a diameter of 8-20 mm.

Example—Cover

In another preferred embodiment of a transcatheter valve, there is provided a feature wherein the cover is comprised of polyester, polyethylene terephthalate, decellularized pericardium, or a layered combination thereof.

Example—Annular Gel Ring

In another preferred embodiment of a transcatheter valve, there is provided a feature wherein the nitinol frame supports a gel ring, wherein the gel ring is comprised of an expandable material enclosed within an outer sealing membrane, wherein the expandable material is a swellable powder within a polymeric matrix, a swellable polymeric matrix, or a swellable polymeric liquid.

Example—Annular Inflatable Ring

In another preferred embodiment of a transcatheter valve, there is provided a feature wherein the nitinol frame supports a deflatable ring, wherein the deflatable ring is comprised of a toroid-shaped sealed compartment having a valve, said sealed compartment fillable with a biocompatible liquid or gas, wherein upon removal of some or all of the biocompatible liquid or gas, the deflatable ring has a reduced diameter, and wherein upon removal of some or all of the biocompatible liquid or gas, the top spacer segment of the cylinder has a reduced height and the collar is compressed in the direction of the top wire frame.

Example—Shaped Flow Control Member

In another preferred embodiment of a transcatheter valve, there is provided a feature wherein the flow control member has an hourglass (hyperboloid) shape from top end to bottom end.

Example—Support Post

In another preferred embodiment of a transcatheter valve, there is provided a feature wherein the bottom end of the sleeve has a sinusoidal edge, and wherein one or more sections of the sleeve edge may be secured to one or more rigid support posts.

Example—Threaded

In another preferred embodiment of a transcatheter valve, there is provided a feature wherein the atrial frame comprises a threaded structure, wherein the threaded structure allows for a simple circular screw-type deployment of the device into a native annulus to aid in sealing and sizing of the top collar into the native annulus.

Example—Method

In a preferred embodiment of the invention, there is also provided a method of controlling flow of bodily fluid within an enclosed cavity of a human body, said enclosed cavity having a reciprocating pressure differential, the method comprising the steps: (i) delivering the transcatheter prosthetic medical device described herein, to the enclosed cavity within the human body; (ii) arranging the prosthetic medical device whereby the flow control member and channel are arranged parallel to a flow of fluid entering the enclosed cavity; (iii) expanding a top frame above an entrance to the enclosed cavity to mount the top end of the flow control member within the entrance, whereby the top flange applies an compression force and seals the entrance, and expanding the bottom frame below the entrance to the enclosed cavity to position the bottom end of the flow control member within the enclosed cavity; wherein bodily fluid arriving at the enclosed cavity is diverted into the channel of the flow control member; wherein the reciprocating pressure differential comprises a low pressure state and a high pressure state; wherein bodily fluid flows into the channel to the enclosed cavity during the low pressure state, and wherein bodily fluid is prevented from flowing into the channel to the enclosed cavity during the high pressure state, wherein the high pressure state exerts a force on the sub-annular or ventricular surface of the flow control member and reversibly collapses the channel.

Delivery Example

The transcatheter prosthetic heart valve may be percutaneously delivered using a transcatheter process via the carotid, but both carotid, femoral, sub-xyphoid, and intercostal access across the chest wall. The device is delivered via catheter to the right or left atrium and is expanded from a compressed shape that fits with the internal diameter of the catheter lumen. The compressed valve is loaded external to the patient into the delivery catheter, and is then pushed out of the catheter when the capsule arrives to the atrium. The cardiac treatment technician visualizes this delivery using available imaging techniques such as fluoroscopy or ultrasound, and in a preferred embodiment the pinch valve self-expands upon release from the catheter since it is constructed in part from shape-memory material, such as Nitinol®, a nickel-titanium alloy used in biomedical implants.

In another embodiment, the valve may be constructed of materials that requires balloon-expansion after the capsule has been ejected from the catheter into the atrium.

Once the atrial collar/frame and the conduit flow control member are expanded to their functional diameter, they is deployed into the native annulus. The optional ventricular collar is expanded below the annulus forming a layered stack with the collars on top and bottom and the native annulus in the middle. It is also contemplated that an optional support post may be deployed within the lumen or within the seam, of the flow control member. Once the frame is deployed about the tricuspid annulus, fasteners secure the device about the native annulus. Additional fastening of the device to a moderator band mounting may be performed, and the deployment is complete. Further adjustments using hemodynamic imaging techniques are contemplated as within the scope of the invention in order to ensure the device is secure, is located and oriented as planned, and is functioning as a substitute or successor to the native tricuspid valve.

Delivery Example

Several suitable delivery and deployment methods are discussed herein and discussed further below; however, one of ordinary skill in the art will recognize a plurality of methods suitable to deliver the prosthesis to the targeted native valve region (e.g., percutaneous, transcatheter delivery using retrograde or antegrade approaches). Additionally, one of ordinary skill in the art will recognize a plurality of methods suitable to deploy the prosthesis from a compressed configuration for delivery to the expanded configuration In the compressed configuration, the prosthesis has a low profile retained as such by a delivery capsule or sheath that together are suitable for delivery through small-diameter guide catheters positioned in the heart via antegrade or retrograde approaches. As used herein, "expanded configuration" refers to the configuration of the prosthesis when allowed to freely expand to an unrestrained size without the presence of constraining or distorting forces. "Deployed configuration," as used herein, refers to the prosthesis once expanded at the native valve site (e.g., subject to the constraining and distorting forces exerted by the native anatomy) and subject to any anchoring or mounting mechanisms or forces.

During deployment, a delivery sheath is retracted proximally exposing the one component of the prosthesis within a first heart chamber or structure. The prosthesis may then be positioned in this partially expanded configuration before fully retracting the delivery sheath to expose the prosthesis in the the deployed configuration. In certain embodiments, the delivery sheath can reengage the prosthesis thereby transitioning the prosthesis from the deployed configuration to the delivery configuration for re-positioning purposes or for complete retrieval and termination of the procedure.

As used in reference to the delivery system, "distal" refers to a position having a distance farther from a handle of the delivery system along the longitudinal axis of the delivery system, and "proximal" refers to a position having a distance closer to the handle of the delivery system along the longitudinal axis of the delivery system.

The delivery system may optionally include a guide catheter having a handle coupled to a delivery shaft, which in some embodiments is 34 F or less in diameter. The guide catheter may be steerable or pre-shaped in a configuration suitable for the particular approach to the target native valve. A delivery catheter is slideably disposed within the guide catheter and includes a flexible tubular outer shaft that extends to a delivery sheath at a distal end. During advancement to a treatment site, the prosthesis is positioned in a compressed or delivery configuration within the delivery sheath.

In one embodiment, a flexible inner shaft may optionally be positioned slideably within outer shaft and extend at least partially through the prosthesis.

The prosthesis is coupled to guide wires or to the inner shaft and is released from the guide wires or inner shaft using specific coupling-decoupling features that can be actuated from the proximal end of the delivery system.

In other embodiments in accordance herewith, other guidewire lumens are contemplated such as one that extends the length of the delivery system such that the delivery sheath and/or other catheter thereof may be used in an over-the-wire manner. The delivery sheath can protect and secure the prosthesis in its compressed configuration during delivery. The delivery catheter is coupled to a plurality of actuator mechanisms on the handle of the delivery catheter.

Various actuator mechanisms can be used, such as a ball-and-sleeve release, a bead-and-channel release, a spring-loaded release, an axially-slidable lever, a rotatable rack and pinion gear, or other known mechanisms. This mechanism on the handle allows the operator to manage release wires configured to couple the prosthesis to the delivery catheter. Once deployed, the suitable mechanism can be dis-engaged to retract the release wires in a proximal direction and following device deployment, the delivery catheter and guide catheter can be retracted through the vasculature and removed from the patient.

Image guidance, e.g., intracardiac echocardiography (ICE), fluoroscopy, computed tomography (CT), intravascular ultrasound (IVUS), optical coherence tomography (OCT), or another suitable guidance modality, or combination thereof, may be used to aid the clinician's positioning and manipulation of the prosthesis at the target native valve region. In some embodiments, image guidance components (e.g., IVUS, OCT) can be coupled to the distal portion of the delivery catheter, guide catheter, or both to provide three-dimensional images of the vasculature proximate to the target heart valve region to facilitate positioning and/or deployment of the prosthesis within the heart valve region.

Drawings

Figure 1:
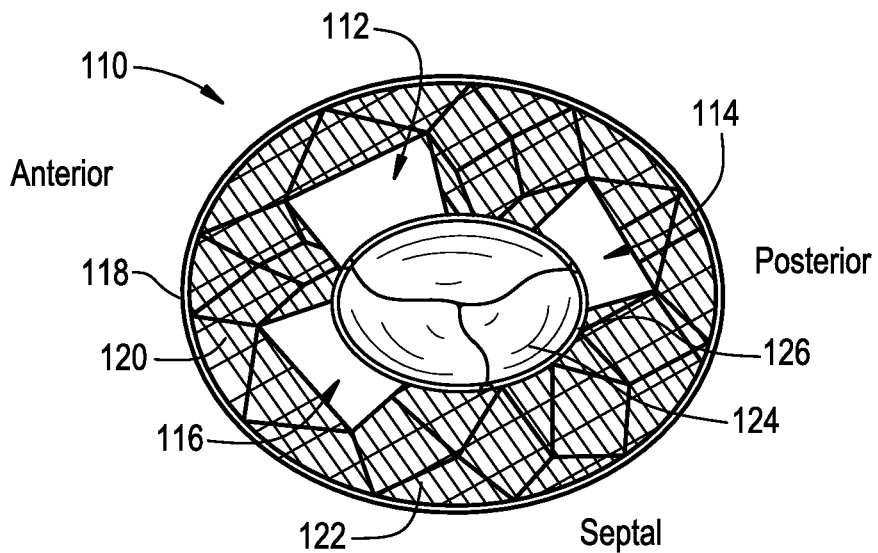

Referring now to the drawings, FIG. 1 is an illustration of a top view of a heart valve prosthesis 110 according to the present invention. FIG. 1 shows polyester mesh covering 122 a valve frame 120 encircling a collapsible flow control member 124 and wherein the valve frame 120 has meshless windows 112 114 116 or tissue-capturing plication gaps. FIG. 1 shows the plication windows 112-114-116 as rectangular windows but the invention contemplates any shape that will facilitate capture and plication of annular tissue. FIG. 1 also shows the flow control member (FCM) 124 coapting to form a three panel closure. FIG. 1 also shows the frame 120 having Nitinol wire frame in diamond shapes with a biocompatible covering. In one embodiment, the frame may have a pericardial material on top and a polyester material, e.g. surgical Dacron®, underneath to be in contact with the native annulus and promote ingrowth.

Figure 2A:
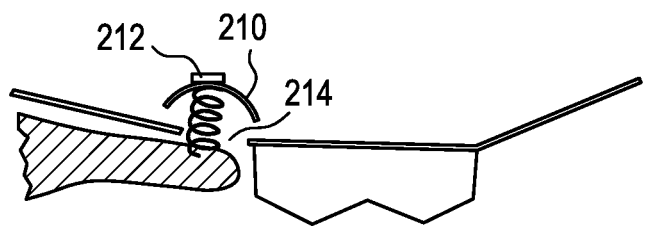
Figure 2D:
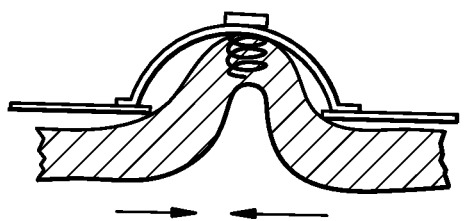
Figure 2B:
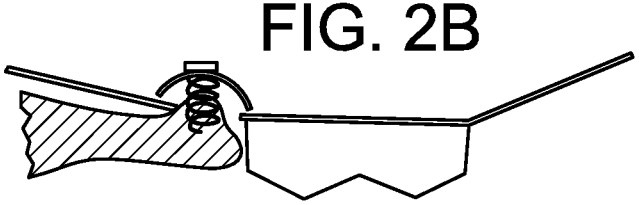
Figure 2C:
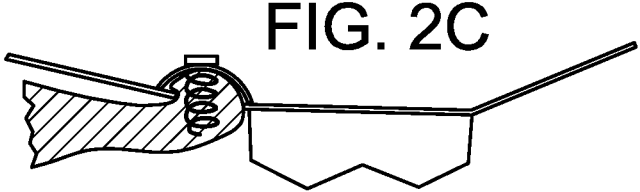

FIG. 2(a)-(d) is an illustration of a plan view of a plication dome 210 on a heart valve prosthesis according to the present invention. FIG. 2(a) shows a tissue anchor 212 accessing annular tissue through the plication window 214. FIG. 2(b) shows the tissue anchor being actuated or rotated to advance into the annular tissue and raising the annular tissue up and through the plication window. FIG. 2(c) shows the tissue anchor completing the plication of the annular tissue into the plication window. FIG. 2(d) shows a cross-sectional view of the plicated annular tissue pulled into the plication window and dome using the plication tissue anchor. FIG. 2(d) shows how the annulus tissue is circumferentially foreshortened.

It is contemplated that the tissue anchor may be a helical coil or screw having a head with a hex connector that is remotely actuated using a guide wire having a hex tool fitted at a distal end.

Figure 3A:
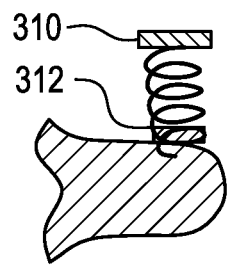
Figure 3B:
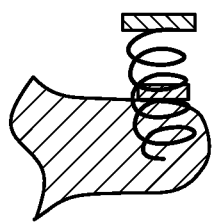
Figure 3C:
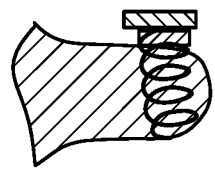

FIG. 3(a)-(c) is an illustration of a plan view of a tissue anchor 310 having a floating radio-opaque marker 312. FIG. 3(a) shows the tissue anchor accessing the annular tissue with the radio-opaque marker at the distal end of the anchor and in contact with the atrial surface of the annular tissue. FIG. 3(b) shows the tissue anchor advancing into the annular tissue with the radio-opaque marker threaded onto the tissue anchor and maintaining position on the atrial surface of the annular tissue. FIG. 3(c) shows the tissue anchor completely advanced into the annular tissue such that the tissue anchor and the threaded floating marker are now adjacent, indicating the desired depth, tension, and/or plication of the tissue anchor with respect to the annular tissue.

Figure 4:
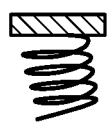
FIG. 4 is an illustration of a plan view of of a tissue anchor having a straight thread and a constant pitch.

FIG. 4 is an illustration of a plan view of of a tissue anchor having a straight thread and a constant pitch.

Figure 5:
FIG. 5 is an illustration of a plan view of of a tissue anchor having a straight thread and a variable pitch.

FIG. 5 is an illustration of a plan view of of a tissue anchor having a straight thread and a variable pitch.

Figure 6:
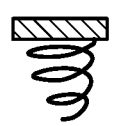
FIG. 6 is an illustration of a plan view of of a tissue anchor having a tapered thread and a constant pitch.

FIG. 6 is an illustration of a plan view of of a tissue anchor having a tapered thread and a constant pitch.

Figure 7:
FIG. 7 is an illustration of a plan view of of a tissue anchor having a sunken taper thread and a variable pitch.

FIG. 7 is an illustration of a plan view of of a tissue anchor having a sunken taper thread and a variable pitch.

FIG. 8(a)-(d) is an illustration of a plan view of heart valve prosthesis according to the invention having a laddered plication dome 810. FIG. 8(a) shows a tissue anchor 814 accessing annular tissue through a plication window in the cuff frame with the head of the tissue anchor engaged in a lower rung of an anchor ladder 812. FIG. 8(b) shows a tissue anchor accessing annular tissue through a plication window in the cuff frame with the head of the tissue anchor advancing up the anchor ladder and engaged in a middle rung of the anchor ladder. FIG. 8(c) shows a tissue anchor accessing annular tissue through a plication window in the cuff frame with the head of the tissue anchor advancing up the anchor ladder and engaged in a top rung of an anchor ladder. FIG. 8(d) shows a cross-sectional view of the plicated annular tissue pulled into the plication window and dome using the plication tissue anchor. FIG. 8(d) shows how the annulus tissue is circumferentially foreshortened.

FIG. 9 is an illustration of a plan view of catheter deployment through the inferior vena cava of a heart valve prosthesis according to the present invention. FIG. 9 shows guide wire 912 advanced in the right ventricle with the heart valve prosthesis 910 being ejected from the distal end of the catheter 914.

FIG. 10 is an illustration of a plan view of catheter deployment through the inferior vena cava of a heart valve prosthesis 1010 according to the present invention. FIG. 10 shows guide wire 1012 advanced in the right ventricle with the heart valve prosthesis 1010 deployed in the tricuspid annulus, and a plication dome 1016 is advanced from the distal end of the catheter 1014 towards a plication window 1018 in the cuff/flange 1020.

FIG. 11(a)-(b) is an illustration of a plan view of catheter deployment through the inferior vena cava of a heart valve prosthesis according to the present invention. FIG. 11(a) shows guide wire advanced in the right ventricle with the heart valve prosthesis deployed in the tricuspid annulus, and a plication dome is mounted on a plication window in the cuff/flange using control cable 1130, with inset showing tissue anchor advancing into the atrial surface of the annular tissue. FIG. 11(b) shows a close-up detail view of a plication dome 1116 over a valve atrial cuff 1120 with a tissue anchor 1112 inserted into native annular tissue.

FIG. 12 is an illustration of a plan view of catheter deployment through the inferior vena cava of a heart valve prosthesis according to the present invention. FIG. 12 shows the control wire for the plication dome being withdrawn and the plication dome mounted on a plication window in the cuff/flange, with tissue anchor advanced into the atrial surface of the annular tissue.

FIG. 13 is an illustration of a perspective view of a heart valve prosthesis according to the present invention deployed within the tricuspid annulus. FIG. 13 shows a plication dome 1316 and 3 topologically diverse tissue anchors 1340 1341 1342 mounting the heart valve prosthesis to the annular tissue.

FIG. 14 is an illustration of a top view of a heart valve prosthesis according to the present invention deployed within the tricuspid annulus. FIG. 14 shows a plication dome 1410 and 3 topologically diverse tissue anchors 1412-1414-1416 mounting the heart valve prosthesis to the annular tissue.

FIG. 15 is an illustration of a cross-sectional plan view of a heart valve prosthesis 1510 according to the present invention. FIG. 15 shows a plication dome 1516 and 3 topologically diverse tissue anchors 1540 1541 1542 mounting the heart valve prosthesis 1510 to the annular tissue (not shown). Valve frame 1528 is shown adjacent to and supporting valve leaflet structure 1524.

FIG. 16 is an illustration of a perspective view of a heart valve prosthesis 1610 according to the present invention deployed within the tricuspid annulus. FIG. 16 shows a plication dome 1616 and 2 topologically diverse tissue anchors 1640 1641 mounting the cuff 1620 of the heart valve prosthesis 1610 to the annular tissue. FIG. 16 shows valve frame 1628 spanning the annulus with sub-annular lower cuff 1626 and valve leaflet member 1624.

FIG. 17 is an illustration of a perspective view of a heart valve prosthesis according to the present invention having a upper cuff 1718 with three uncovered plication windows 1712-1714-1716 and a central aperture having the collapsible flow control member (FCM) 1724 disposed therein and providing an axial tube valve. FIG. 17 also shows wire frame 1720 and covering 1722, as well as lower flange 1728.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

Having described embodiments for the invention herein, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters Patent is set forth in the appended claims.

The invention claimed is:

1. A transcatheter heart valve replacement comprising:
    an asymmetric wire frame with an upper angled collar of scalloped diamond-shape cells forming an atrial flange, wherein the atrial flange has a steep angle of inclination at a septal region of the wire frame, and a shallower angle of inclination around anterior and posterior annular regions of the wire frame, and
    a lower transannular member defining a lumen connected to the atrial flange, the lower transannular member comprised of a plurality of diamond-shape cells, wherein the wire frame has an inner covering of pericardial tissue, and an outer covering of a polyester material;
    a reciprocating flow control member mounted on the lower transannular member and disposed within the lumen;
    wherein the upper angled collar having from 1-8 windows, each window having a tissue anchor disposed therein for engaging annular tissue through the window; and,
    a plurality of secondary tissue anchors, each secondary tissue anchor mounted on the wire frame for engaging annular tissue.

2. The transcatheter heart valve replacement of claim 1, wherein there is a second lower angled collar of scalloped diamond shapes forming a sub-annular ventricular flange.

3. The transcatheter heart valve replacement of claim 1, wherein the steep angle is between 30-90 degrees to the horizontal plane of the annulus.

4. The transcatheter heart valve replacement of claim 1, wherein the tissue anchor comprises a floating radio-opaque marker threaded onto the tissue anchor, wherein advancing the tissue anchor through tissue moves the floating radio-opaque marker from an initial distal lower thread position on the anchor to a secondary position on a higher thread.

5. The transcatheter heart valve replacement of claim 4, wherein one or more of the tissue anchors or the secondary tissue anchors are selected from the group consisting of: a straight thread constant pitch fastener, a tapered thread constant pitch fastener, a straight thread variable pitch fastener, a tapered thread variable pitch fastener, and a sunken taper thread variable pitch fastener.

6. The transcatheter heart valve replacement of claim 4, wherein the atrial flange is configured as a flat cone shape, the atrial flange having an outer diameter R of 50-70 mm, the flow control member having an inner diameter r of 20-30 mm, and the transcatheter heart valve replacement having a height of 20-40 mm.

7. The transcatheter heart valve replacement of claim 4, wherein the cuff frame has an inner wall and an outer wall, said inner wall having a biocompatible material comprising pericardial tissue, and said outer wall having a biocompatible material comprising a woven synthetic polyester material.

8. The transcatheter heart valve replacement of claim 4, wherein the window is an uncovered aperture.

9. The transcatheter heart valve replacement of claim 4, wherein the window is covered by either pericardial tissue or a woven synthetic polyester material.

10. The transcatheter heart valve replacement of claim 4, wherein the wire frame is configured as an hourglass flat conical shape, the atrial flange having a top diameter R1 of 50-70 mm, the lower transannular member having a bottom diameter R2 of 50-70 mm, the flow control member having an internal diameter r of 20-30 mm, and the transcatheter heart valve replacement having a height of 20-50 mm.

11. The transcatheter heart valve replacement of claim 4, wherein the flow control member has an internal diameter of 20-30 mm, said flow control member comprising three substantially flat rectangular panels of pericardial material joined to form a rounded triangular cylinder.

12. The transcatheter heart valve replacement claim 4, wherein the transcatheter heart valve replacement is compressible and fits when compressed within the internal diameter of a transcatheter implantation catheter having an internal diameter less than 22 Fr (7.33 mm) to 34 Fr (9.33 mm).

13. The transcatheter heart valve replacement of claim 4, wherein the flow control member is supported with one or more longitudinal supports integrated into a fabric or material of the flow control member, the one or more longitudinal supports selected from rigid or semi-rigid ribs, rigid or semi-rigid battons, rigid or semi-rigid panels, and combination thereof.

14. The transcatheter heart valve replacement of claim 4, wherein one or more of the tissue anchors or secondary tissue anchors are selected from the group consisting of: a helical coil, a screw, a dart, a pin, and a fastener means.

15. A method for securing a transcatheter heart valve prosthesis within a heart, the method comprising the steps:
(i) advancing a procedure guide wire into a ventricle of a heart;
(ii) advancing a 22 Fr-34 Fr steerable catheter over the procedure guide wire to deliver a compressed transcatheter heart valve prosthesis to an atrium of the ventricle of the heart;
(iii) advancing the catheter to the valve annulus and releasing the self-expanding atrial sealing collar from within the catheter;
(iv) advancing a tissue anchor to a window of the cuff frame;
(v) anchoring a tissue anchor through the window and into the annular tissue; and
(vi) withdrawing the guide wire and steerable catheter from the heart,
wherein the transcatheter heart valve prosthesis comprises an asymmetric wire frame with an upper angled collar of scalloped diamond-shape cells forming an atrial flange and a lower angled collar of scalloped diamond shapes forming a sub-annular ventricular flange,
wherein the atrial flange has a steep first angle of inclination at a septal region of the wire frame, and a shallower second angle of inclination around anterior and posterior annular regions of the wire frame,
wherein the atrial flange has an outer diameter of 50-70 mm and
a lower transannular member defining a lumen connected to the atrial flange, the lower transannular member comprised of a plurality of diamond-shape cells, wherein the wire frame has an inner covering of pericardial tissue, and an outer covering of a polyester material;
a reciprocating flow control member mounted on the lower transannular member and disposed within the lumen,
wherein the flow control member has an inner diameter of 20-30 mm;
wherein the upper angled collar having from 1-8 windows, each window having a tissue anchor disposed therein for engaging annular tissue through the window; and,
a plurality of secondary tissue anchors, each secondary tissue anchor mounted on the wire frame for engaging annular tissue,
wherein the transcatheter heart valve prosthesis has a height of 20-40 mm;
wherein the transcatheter heart valve replacement is compressible and fits when compressed within the internal diameter of a transcatheter implantation catheter having an internal diameter less than 22 Fr (7.33 mm) to 34 Fr (9.33 mm).

16. The method of claim 15, wherein the window is an uncovered aperture.

17. The method of claim 15, wherein the window is covered by either pericardial tissue or a woven synthetic polyester material.

* * * * *